United States Patent [19]
Chan et al.

[11] Patent Number: 5,032,389
[45] Date of Patent: Jul. 16, 1991

[54] ZINC TRIPOLYPHOSPHATE COMPOUNDS AS ANTICALCULUS AND ANTIPLAQUE AGENTS

[75] Inventors: Albert S. Chan, St. Louis; John R. Wiedemann, Fenton, both of Mo.; Samuel L. Hull, Granite City, Ill.

[73] Assignee: Monsanto Chemical Company, St. Louis, Mo.

[21] Appl. No.: 425,092

[22] Filed: Oct. 23, 1989

[51] Int. Cl.$^5$ .............................................. A61K 7/16
[52] U.S. Cl. ................................................ 424/57
[58] Field of Search ......................................... 424/57

[56] References Cited

U.S. PATENT DOCUMENTS 3,105,798 10/1963 Holiday et al. .................. 167/93
3,642,979 2/1972 Irani ................................. 424/54
3,696,191 10/1972 Weeks .............................. 424/50

OTHER PUBLICATIONS

Cosmetic Science, vol. 1, Academic Press: New York, 1978, pp. 1-37 "Cosmetics and Dental Health", G. B. Winter, J. J. Murray, L. Shaw.

Primary Examiner—Shep K. Rose
Attorney, Agent, or Firm—Lawrence L. Limpus

[57] ABSTRACT

A dentifrice composition is disclosed which contains an effective amount of a zinc-alkali metal tripolyphosphate compound for the control of dental plaque and dental calculus.

18 Claims, No Drawings

ZINC TRIPOLYPHOSPHATE COMPOUNDS AS ANTICALCULUS AND ANTIPLAQUE AGENTS

BACKGROUND OF THE INVENTION

This invention relates to a dentifrice composition having improved efficiency in the control of dental calculus and dental plaque.

More particularly, this invention relates to a dentifrice composition containing zinc salts whereby such composition is more effective in controlling both dental calculus and dental plaque.

More particularly, this invention relates to a dentifrice composition wherein effective amounts of a preferred zinc salt, zinc sodium tripolyphosphate salt, are blended into the dentifrice composition to provide a dentifrice composition having significantly better control of both dental calculus and dental plaque.

This invention also relates to methods for controlling dental plaque and dental calculus.

DESCRIPTION OF THE PRIOR ART

From a cosmetic point of view, probably the most important aspect of dental health is the color and integrity of a person's teeth. Sparkling white teeth are generally considered esthetically pleasing, whereas discolored, decayed, and broken down teeth are socially disadvantageous. While it has been found that adequate cleansing of the teeth can be achieved by the use of a toothbrush alone, most individuals require some abrasive to assist in removing materials that tend to accumulate on the teeth. The primary objective in using a dentifrice, or toothpaste, is to aid the cleansing of accessible tooth surfaces and to make tooth brushing more pleasant. The most important constituents of a toothpaste in relation to its mechanical cleansing properties are the abrasives and the surface active agents. Many therapeutic agents have been added to dentifrices in an effort to improve their cleaning power and to help reduce inflammation.

Dental plaque, which mainly consists of aggregations of bacteria and their products on the tooth surface, produces acid in the presence of sucrose and, if the tooth surface is susceptible, dental caries results. If the teeth can be kept scruptiously clean and free from plaque, very few lesions occur, although it is doubtful whether the average person can achieve a situation where plaque is completely absent from their mouth. Bacteria, fungi, desquamated epithelial cells and food debris accumulate on the tooth surface and, in the absence of mechanical tooth cleaning procedures, a bacterial plaque is formed. Since dental plaque is the ultimately important factor causing periodontal disease, preventive methods should aim at its removal and reduction in its formation. Plaque develops even in the absence of food in the mouth; the consistency and type of diet affects only the quantity and biochemistry of the developing plaque. If plaque is allowed to remain in the mouth for long periods, it may calcify and be converted into calculus.

G. B Winter, J. J. Murray, and L. Shaw reported in *Cosmetic Science*, edited by M. M. Breuer, Academic Press, New York 1978 (pages 1-37) that "Nearly 40 substances with potential therapeutic activity have been incorporated in dentifrice formulations." The majority of them are specifically antiplaque agents. Many others have been incorporated into mouth rinses but not into a dentifrice. Among the substances which have been used are fluorides, antibiotics, surface active agents, enzymes and crystal growth inhibitors. They also reported that anti-calculus and anti-plaque actively was claimed for the use of zinc salts; however, the clinical trials primarily tested the benefits of zinc salts added to mouthwashes. The disclosed tests specifically used zinc acetate in a dentifrice and benzethonium and zinc chloride in mouthwashes.

The Procter and Gamble Company introduced a tarter control toothpaste in 1986. This toothpaste contained a mixture of tetrasodium pyrophosphate and sodium acid pyrophosphate.

SUMMARY OF THE INVENTION

This invention is directed to a new dentifrice composition having improved efficiency in the control of dental calculus and dental plaque. An amount of an inorganic mixed zinc salt effective for control dental calculus and dental plaque is blended into the dentifrice to provide a more effective composition. The mixed zinc salts may be employed with any suitable polishing agent whether in paste or gel form such as dicalcium phosphate dihydrate, calcium carbonate, alumina or silica gel.

DESCRIPTION OF THE PREFERRED EMBODIMENTS

Dicalcium phosphate dihydrate, calcium carbonate, and alumina are dental polishing products which are used in paste-type dentifrices. Silica gel is used as a dental polishing agent in gel-type dentifrices. The addition of mixed zinc-alkali metal tripolyphosphate salts such as the preferred zinc sodium tripolyphosphate compounds to the polishing agents in both paste and gel type dentifrices provides a dentifrice with significantly improved control of both dental calculus and dental plaque.

A preferred mixed zinc salt, a zinc-alkali metal tripolyphosphate such as zinc sodium tripolyphosphate with any ratio of zinc to sodium, is blended into the dentifrice in a range of from about 4 ppm to about 10% by weight of the dentifrice, preferably in a range of from about 1.25% to about 5.0% by weight of the dentifrice, and more preferably in a range of from about 1.25% to about 2.5% by weight of the dentifrice.

The use of sodium in the mixed zinc-alkali metal tripolyphosphate compound provides the preferred compound. However, the other alkali metals, potassium, lithium, ammonium, cesium and rubidium, may also be used. The principal function of the alkali metal is to improve the solubility of the zinc salt. Zinc tripolyphosphate is more difficult to produce than the mixed zinc-alkali metal tripolyphosphates and it is of limited use because of its insolubility.

In addition to the abrasive or polishing agent, both paste and gel type dentifrice compositions will contain a source of fluoride ions and any of the commonly used other ingredients of a dentifrice composition. The commonly used other ingredients include flavoring substances, sudsing agents, thickening agents, humectants and a suitable coloring agent. A dicalcium phosphate dihydrate based dentifrice composition will contain, for example, dicalcium phosphate dihydrate as a polishing agent, a source of fluoride ions, and any of the commonly used other ingredients of a dentifrice composition including flavoring substances such as esters and the oils of wintergreen, peppermint and spearmint; sudsing agents such as water-soluble alkyl and alkyl-ether sulfates and sulfonates having alkyl groups of from about 8 to 18 carbon atoms, water-soluble salts of sulfonated monoglycerides of fatty acids having from 10 to 18 carbon atoms, water-soluble salts of sulfated fatty alcohols having from 10 to 18 carbon atoms, salts of fatty acid esters of isethionic acid, and salts of fatty acid amides of taurines; thickening agents such as water-soluble salts of cellulose ethers such as sodium carboxymethyl cellulose, natural gums and colloidal magnesium aluminum silicate or finely divided silica; humectants such as glycerine, sorbitol and other polyhydric alcohols; and suitable coloring agents, if desired.

Two zinc sodium tripolyphosphate compounds have been found to be highly effective in the inhibition of the growth of the microbes Streptococcus Mutan and Lactobacellus Casei which are thought to contribute to the formation of dental caries and plaque. Both zinc compounds have also been found to be effective in the inhibition of the precipitation of calcium phosphates which are thought to be one of the causes of dental calculus formation. The zinc sodium tripolyphosphate compounds which have been found to be highly effective are $Zn_2NaP_3O_{10}\cdot 9H_2O$ and $ZnNa_3P_3O_{10}\cdot 12H_2O$, and a mixture of these two compounds. An advantage from the use of zinc sodium tripolyphosphates in a dentifrice is that the pH of the slurries that are created is close to neutral. This is important as oral products desirably have a neutral pH.

The zinc sodium tripolyphosphate salts may be prepared according to the following reactions:

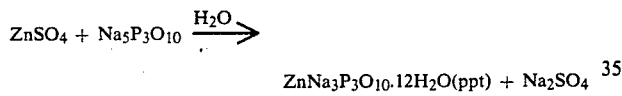

$$ZnSO_4 + Na_5P_3O_{10} \xrightarrow{H_2O} ZnNa_3P_3O_{10}\cdot 12H_2O(ppt) + Na_2SO_4$$

and

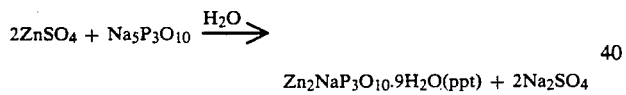

$$2ZnSO_4 + Na_5P_3O_{10} \xrightarrow{H_2O} Zn_2NaP_3O_{10}\cdot 9H_2O(ppt) + 2Na_2SO_4$$

The first of these materials, $ZnNa_3P_3O_{10}\cdot 12H_2O$, is about 20 times more soluble than the second, $Zn_2NaP_3O_{10}\cdot 9H_2O$. Analyses of saturated solutions of each have shown 1022 ppm and 58 ppm zinc, respectively.

Two tests were chosen to demonstrate the effectiveness of the zinc sodium tripolyphosphate compounds. The first test demonstrated the effect of the zinc compounds on the inhibition of the growth of two microbes, Streptococcus Mutan and Lactobacillus Casei, which are thought to contribute to dental caries and dental plaque. The second test demonstrated the threshold concentration of zinc sodium tripolyphosphate compound which will inhibit the precipitation of calcium phosphates which are thought to be on of the causes of the formation of calculus deposits on the teeth.

The invention will be better understood by the following examples which illustrate, but do not limit, the preparation and effectiveness of compositions of this invention.

EXAMPLE 1

The following tests were performed to demonstrate the effectiveness of the compounds of this invention in inhibiting the growth of the microbes which are believed to be the cause of dental plaque. Two test organisms were prepared for this example, Lactobacillus Casei (L. Casei, ATCC-393) and Streptococcus Mutan (S. Mutan, ATCC-25175). Test cultures of L. Casei were grown on Microassay Agar produced by Difco Laboratories and test cultures of S. Mutan were grown on Brain Heart Infusion Agar which is also produced by Difco Laboratories. The organisms were culture grown at 37° C. for 24 hours and were then diluted with nine times sterile water. The correspondding Agars were used to support each test culture in the microbial growth inhibition studies. Initially a 10% mixture was prepared by mixing 18 grams of sterile agar thoroughly with 2 grams of the test compound, zinc sodium tripolyphosphate. Other concentrations of zinc sodium tripolyphosphate compound were obtained by further diluting this agar mixture with additional sterile agar. The mixture of sterile agar and zinc sodium tripolyphosphate compounds was poured into sterile petri dishes and allowed to solidify. One drop of the test organism, L. Casei or S. Mutan, was placed on the surface of the solidified agar and the petri dishes were inverted and placed in an oven where they were maintained at a temperature of 37° C. for 48 hours. After the incubation period, the contents of the petri dishes were examined for signs of microbial growth. Any growth would indicate that the test compound was not effective at the zinc concentration used in that petri dish. The results of the microbial growth inhibition studies are shown in Table 1 where ZSTP is used to represent zinc sodium tripolyphosphate.

TABLE 1

| Concentration of ZSTP | $Zn_2NaP_3O_{10}\cdot 9H_2O$ | | $ZnNa_3P_3O_{10}\cdot 12H_2O$ | |
| --- | --- | --- | --- | --- |
| | S. Mutan | L. Casei | S. Mutan | L. Casei |
| 10% | X | X | X | X |
| 5% | X | X | X | X |
| 2.5% | X | X | X | X |
| 1.25% | X | O | X | X |
| 1.00% | O | O | O | O |

X = Effective against microbial growth.
O = Not-effective against microbial growth.

EXAMPLE 2

In addition to the microbial growth inhibition effect, zinc sodium tripolyphosphate compounds have also been found to be effective in the threshold inhibition of the precipitation of calcium phosphates. The precipitation and crystallization of calcium phosphate at the surface of teeth is generally considered to be part of the reason for dental calculus formation. This problem can be alleviated by using an inhibitor to reduce or prevent the calcium phosphate precipitation. The critical concentrations of the test compounds, that is the zinc sodium tripolyphosphate compounds, for the threshold inhibition of calcium phosphate precipitation were determined by using the following procedure in which the in-vitro calcium phosphate precipitation tests were conducted under simulated oral conditions at 37° C. (body temperature). The calcium (80 ppm), phosphorus (155 ppm) sodium (460 ppm), potassium (460 ppm) and chloride (1270 ppm) levels and ionic strength (0.048 molar) level of the solutions used in the tests are the average observed levels in human saliva. Each prepared solution was observed for a period of three hours to determine whether precipitation of calcium phosphate occurred. The three hour period of time was selected as being representative of human oral processes. When the calcium phosphate precipitation begins, the pH of the solution decreases abruptly from a pH of 7.0 to 7.2 to approximately a pH of 6.7. Since the measurement of pH was more sensitive to the initiation of precipitation than visual observation of the initial changes in turbidity caused by marginal precipitation, both the measurement of pH and visual observation were used to determine the effect of the use of inhibitors to prevent the precipitation of calcium phosphate.

STOCK SOLUTIONS

Several stock solutions were prepared for use in the precipitation tests:

A. A calcium solution was prepared by dissolving 14.7 grams (0.1M) $CaCl_2.2H_2O$, 58.4 grams (1M) sodium chloride (NaCl) and 37.3 grams (0.5M) potassium chloride (KCl) in about 800 milliliters water. The pH of the solution was adjusted to a pH of 7.0 by the addition of an appropriate amount of sodium hydroxide solution (NaOH) and the calcium solution was diluted to one liter.

B. A phosphate solution was prepared by dissolving 22.82 grams (0.1M) $K_2HPO_4.3H_2O$ and 3 grams (ca.0.03M) concentrated hydrochloric acid solution in one liter of water. The solution had a pH of 7.1.

C. A first zinc sodium tripolyphosphate solution ($ZnNa_3P_3O_{10}$) was prepared by dissolving 0.2 grams zinc sodium tripolyphosphate ($ZnNa_3O_{10}.12H_2O$) in one liter of water. The solution had a pH of 7.1.

D. A second zinc sodium tripolyphosphate solution ($Zn_2NaP_3O_{10}$) was prepared by dissolving 0.2 grams zinc sodium tripolyphosphate ($Zn_2NaP_3O_{10}.9H_2O$) in one liter of water. The pH of the solution was adjusted to a pH of 7.0 by the addition of an appropriate amount of 0.1N sodium hydroxide (NaOH).

CONTROL SOLUTION

A control solution was prepared by adding two milliliters of the calcium solution to a container containing 93 milliliters deionized water. Five milliliters of the phosphate solution were then added while the solution was manually stirred. The solution was immediately incubated for three hours in a 37° C.±1° C. bath that was mildly agitated and it was observed during the incubation. Within about ten to twenty minutes the solution became cloudy and within two to three hours the calcium phosphate coagulated to a fine-grained precipitate. At the end of three hours the measured pH of the solution was 6.7.

TEST SOLUTIONS

Additional solutions were prepared using the same procedure as was used to prepare the control solution. Various amounts of the first and second zinc sodium tripolyphosphate solutions, and mixtures of the solutions, were added to the additional solutions to produce solutions containing zinc sodium tripolyphosphate in the parts per million range, which were then incubated for three hours at 37° C.±1° C. The solutions were observed during incubation to determine the critical concentration of zinc sodium tripolyphosphate. The critical concentration is the minimum concentration of the inhibitor, the zinc sodium tripolyphosphate, which will stabilize the resulting solution at a pH of at least 7.0 after three hours of incubation. This is the minimum concentration at which no calcium phosphate precipitation is observed. The critical concentrations of the zinc compounds for the inhibition of calcium phosphate precipitation are shown in Table 2.

TABLE 2

| Compounds tested | Concentration |
| --- | --- |
| $Zn_2NaP_3O_{10}.9H_2O$ | 7 ppm |
| $ZnNa_3P_3O_{10}.12H_2O$ | 4 ppm |

It has been shown above that zinc sodium tripolyphosphate compounds are effective for controlling dental plaque and dental calculus. Thus, a method for controlling dental plaque and dental calculus comprises contacting teeth with a dentifrice containing a zinc-alkali metal tripolyphosphate compound, preferably a zinc sodium tripolyphosphate compound, in an amount effective for controlling dental plaque and dental calculus. More specifically, a method for controlling dental plaque comprises contacting teeth with a dentifrice containing from about 1.25% to about 10% by weight of a zinc sodium tripolyphosphate compound. Similarly, a method for controlling dental calculus comprises contacting teeth with a dentifrice containing from about 4 ppm to about 10% by weight of a zinc sodium tripolyphosphate.

The foregoing description of this invention is not intended as limiting the invention. As will be apparent to those skilled in the art, many variations on and modifications to the embodiments described above may be made without departure from the spirit and scope of this invention.

We claim:

1. A dentifrice composition comprising a polishing agent and from about 2.5% to about 10% of a zinc sodium tripolyphosphate compound effective for the control of dental plaque and dental calculus.

2. The dentifrice composition of claim 1 wherein said zinc sodium tripolyphosphate compound is selected from the group consisting of $Zn_2NaP_3O_{10}.9H_2O$, $ZnNa_3P_3O_{10}.12H_2O$, and mixtures of $Zn_2NaP_3O_{10}.9H_2O$ and $ZnNa_3P_3O_{10}.12H_2O$.

3. The dentifrice composition of claim 2 wherein said composition contains from about 2.5% to about 5.0% by weight zinc sodium tripolyphosphate.

4. A dentifrice paste composition comprising a polishing agent selected from the group consisting of dicalcium phosphate dihydrate, calcium carbonate, and alumina and from about 2.5% to about 10% by weight of a zinc sodium tripolyphosphate compound.

5. The dentifrice composition of claim 4 wherein said zinc sodium tripolyphosphate compound is selected from the group consisting of $Zn_2NaP_3O_{10}.9H_2O$, $ZnNa_3P_3O_{10}.12H_2O$, and mixtures of $Zn_2NaP_3O_{10}.9H_2O$ and $ZnNa_3P_3O_{10}.12H_2O$.

6. The dentifrice composition of claim 5 wherein said composition contains from about 2.5% to about 5.0% by weight zinc sodium tripolyphosphate.

7. A dentifrice gel composiion comprising a silica gel polishing agent and from about 2.5% to about 10% by weight of a zinc sodium tripolyphosphate compound.

8. The dentifrice composition of claim 7 wherein said zinc sodium tripolyphosphate compound is selected from the group consisting of $Zn_2NaP_3O_{10}.9H_2O$, $ZnNa_3P_3O_{10}.12H_2O$, and mixtures of $Zn_2NaP_3O_{10}.9H_2O$ and $ZnNa_3P_3O_{10}.12H_2O$.

9. The dentifrice composition of claim 8 wherein said composition contains from about 2.5% to about 5.0% by weight zinc sodium tripolyphosphate.

10. A dental polishing product for inclusion in a dentifrice comprising a polishing agent and from about 2.5% to about 10% by weight of a zinc sodium tripolyphosphate compound.

11. The dental polishing product of claim 10 wherein said polishing agent is selected from the group consisting of dicalcium phosphate dehydrate, calcium carbonate, alumina and silica gel.

12. The dental polishing product of claim 11 wherein said zinc sodium tripolyphosphate compound is selected from the group consisting of $Zn_2NaP_3O_{10}.9H_2O$, $ZnNa_3P_3O_{10}.12H_2O$, and mixtures of $Zn_2NaP_3O_{10}.9H_2O$ and $ZnNa_3P_3O_{10}.12H_2O$.

13. A dentifrice composition comprising a polishing agent selected from the group consisting of dicalcium phosphate dihydrate, calcium carbonate, alumina, and silica gel and from about 2.5% to about 10% by weight of a zinc-alkali metal tripolyphosphate compound effective for the control of dental plaque and dental calculus.

14. The dentifrice composition of claim 13 wherein said alkali metal is selected from the group consisting of sodium, potassium, lithium, ammonium, cesium and rubidium.

15. A method for controlling dental calculus comprising contacting teeth with a dentifrice comprising a polishing agent and from about 2.5% to about 10% by weight of said dentifrice of a zinc sodium tripolyphosphate compound.

16. The method of claim 15 wherein said zinc sodium tripolyphosphate compound is selected from the group consisting of $Zn_2NaP_3O_{10}.9H_2O$, $ZnNa_3P_3O_{10}.12H_2O$, and mixtures of $Zn_2NaP_3O_{10}.9H_2O$ and $ZnNa_3P_3O_{10}.12H_2O$.

17. A method for controlling dental plaque comprising contacting teeth with a dentifrice comprising a polishing agent and from about 2.5% to about 10% by weight of said dentifrice of a zinc sodium tripolyphosphate compound.

18. The method of claim 17 wherein said zinc sodium tripolyphosphate compound is selected from the group consisting of $Zn_2NaP_3O_{10}.9H_2O$, $ZnNa_3P_3O_{10}.12H_2O$ and mixtures of $Zn_2NaP_3O_{10}.9H_2O$ and $ZnNa_3P_3O_{10}.12H_2O$.

* * * * *